(12) United States Patent
Vietmeier et al.

(10) Patent No.: US 12,427,018 B2
(45) Date of Patent: Sep. 30, 2025

(54) TRANSCATHETER MITRAL VALVE FIXATION CONCEPTS

(71) Applicant: St. Jude Medical, Cardiology Division, Inc., St. Paul, MN (US)

(72) Inventors: Kristopher Henry Vietmeier, Monticello, MN (US); Theodore Paul Dale, Corcoran, MN (US); Brian Joseph Perszyk, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 193 days.

(21) Appl. No.: 17/222,198

(22) Filed: Apr. 5, 2021

(65) Prior Publication Data
US 2021/0346153 A1 Nov. 11, 2021

Related U.S. Application Data

(60) Provisional application No. 63/022,647, filed on May 11, 2020.

(51) Int. Cl.
*A61F 2/24* (2006.01)
(52) U.S. Cl.
CPC .......... *A61F 2/2418* (2013.01); *A61F 2/2436* (2013.01); *A61F 2220/0016* (2013.01);
(Continued)
(58) Field of Classification Search
CPC ............................ A61F 2/2418; A61F 2/2409
See application file for complete search history.

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| DE | 19857887 A1 | 7/2000 |
| DE | 10121210 B4 | 11/2005 |

(Continued)

OTHER PUBLICATIONS

"Catheter-Implanted Prosthetic Heart Valves: Transluminal Catheter Implantation of a New Expandable Artificial Heart Valve in the Descending Thoracic Aorta in Isolated Vessels and Closed Chest Pigs", Knudsen et al., The International Journal of Artificial Organs, vol. 16, No. 5, May 1993, pp. 253-262.

(Continued)

*Primary Examiner* — Jacqueline Wozniki
(74) *Attorney, Agent, or Firm* — SLEMAN & LUND LLP

(57) ABSTRACT

A prosthetic heart valve includes stabilization features for anchoring the prosthetic heart valve within a native valve annulus. The prosthetic heart valve includes an expandable stent having an inflow end and an outflow end, and a valve assembly disposed within the stent. One such stabilization feature is a collapsible and an expandable frame formed of compliant wires. The frame has a body including a first end coupled to the stent, a second end, and a lumen extending therethrough for receiving the stent and the valve assembly. When the frame is expanded in the native valve annulus, the compliant wires form an indented region in the frame between the first and second ends of the body and a sub-annulus portion of the frame forms a bulge.

12 Claims, 4 Drawing Sheets

(52) U.S. Cl.
CPC .............. *A61F 2220/0025* (2013.01); *A61F 2220/0083* (2013.01)

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,857,845 B2 | 12/2010 | Stacchino et al. |
| 7,914,569 B2 | 3/2011 | Nguyen et al. |
| 8,016,877 B2 * | 9/2011 | Seguin ............... A61F 2/2412 |
| | | 623/1.24 |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,163,007 B2 * | 4/2012 | Dierking ............... A61F 2/95 |
| | | 623/1.36 |
| D660,432 S | 5/2012 | Braido |
| D660,433 S | 5/2012 | Braido et al. |
| D660,967 S | 5/2012 | Braido et al. |
| D684,692 S | 6/2013 | Braido |
| 8,840,661 B2 | 9/2014 | Manasse |
| 8,840,663 B2 | 9/2014 | Salahieh et al. |
| 2002/0002401 A1 * | 1/2002 | McGuckin, Jr. ...... A61F 2/2475 |
| | | 623/1.36 |
| 2002/0022853 A1 * | 2/2002 | Swanson ............... A61F 2/88 |
| | | 623/1.36 |
| 2002/0036220 A1 | 3/2002 | Gabbay |
| 2002/0123790 A1 * | 9/2002 | White ..................... A61F 2/07 |
| | | 623/1.36 |
| 2003/0023303 A1 | 1/2003 | Palmaz et al. |
| 2003/0050694 A1 | 3/2003 | Yang et al. |
| 2003/0083679 A1 * | 5/2003 | Grudem ............... A61B 17/11 |
| | | 623/1.36 |
| 2003/0130726 A1 | 7/2003 | Thorpe et al. |
| 2003/0199987 A1 * | 10/2003 | Berg ................... A61B 17/064 |
| | | 623/1.36 |
| 2004/0049262 A1 | 3/2004 | Obermiller et al. |
| 2004/0093075 A1 | 5/2004 | Kuehne |
| 2004/0210304 A1 | 10/2004 | Seguin et al. |
| 2004/0260394 A1 * | 12/2004 | Douk ................... A61F 2/2433 |
| | | 606/153 |
| 2005/0096726 A1 | 5/2005 | Sequin et al. |
| 2005/0096731 A1 * | 5/2005 | Looi ................... A61L 31/146 |
| | | 435/402 |
| 2005/0137695 A1 | 6/2005 | Salahieh et al. |
| 2005/0137697 A1 | 6/2005 | Salahieh et al. |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0122684 A1 * | 6/2006 | Lye ......................... A61F 2/07 |
| | | 623/1.36 |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 * | 2/2007 | Seguin ............... A61F 2/2433 |
| | | 623/2.11 |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0198097 A1 | 8/2007 | Zegdi |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0255395 A1 * | 11/2007 | Pollock ................. A61F 2/848 |
| | | 623/1.1 |
| 2007/0288087 A1 | 12/2007 | Fearnot et al. |
| 2008/0021544 A1 * | 1/2008 | Majercak ............... A61F 2/848 |
| | | 623/1.36 |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |

(56) References Cited

U.S. PATENT DOCUMENTS

| | | | |
|---|---|---|---|
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0099653 A1 | 4/2009 | Suri et al. | |
| 2009/0112309 A1 | 4/2009 | Jaramillo et al. | |
| 2009/0138079 A1 | 5/2009 | Tuval et al. | |
| 2009/0216310 A1* | 8/2009 | Straubinger | A61F 2/2418 623/1.26 |
| 2010/0004740 A1 | 1/2010 | Seguin et al. | |
| 2010/0036479 A1* | 2/2010 | Hill | A61F 2/2418 623/1.26 |
| 2010/0036484 A1 | 2/2010 | Hariton et al. | |
| 2010/0049306 A1 | 2/2010 | House et al. | |
| 2010/0087907 A1 | 4/2010 | Lattouf | |
| 2010/0131055 A1 | 5/2010 | Case et al. | |
| 2010/0168778 A1 | 7/2010 | Braido | |
| 2010/0168839 A1 | 7/2010 | Braido et al. | |
| 2010/0185277 A1 | 7/2010 | Braido et al. | |
| 2010/0191320 A1* | 7/2010 | Straubinger | A61F 2/2418 623/1.26 |
| 2010/0191326 A1 | 7/2010 | Alkhatib | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0249911 A1 | 9/2010 | Alkhatib | |
| 2010/0249923 A1 | 9/2010 | Alkhatib et al. | |
| 2010/0286768 A1 | 11/2010 | Alkhatib | |
| 2010/0298931 A1 | 11/2010 | Quadri et al. | |
| 2011/0029072 A1 | 2/2011 | Gabbay | |
| 2011/0208298 A1* | 8/2011 | Tuval | A61F 2/2418 623/2.17 |
| 2012/0303116 A1 | 11/2012 | Gorman, III et al. | |
| 2012/0323309 A1* | 12/2012 | Cattaneo | A61F 2/915 623/1.24 |
| 2013/0304200 A1* | 11/2013 | McLean | A61F 2/2412 623/2.18 |
| 2016/0228244 A1* | 8/2016 | Cerf | A61F 2/2418 |
| 2016/0278923 A1* | 9/2016 | Krans | A61F 2/2469 |
| 2017/0049564 A1 | 2/2017 | Board et al. | |
| 2017/0325945 A1* | 11/2017 | Dale | A61F 2/2412 |
| 2020/0113683 A1 | 4/2020 | Dale et al. | |
| 2021/0068950 A1* | 3/2021 | Quill | A61F 2/2427 |
| 2023/0090160 A1* | 3/2023 | Dale | A61F 2/2418 |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1926455 A2 | 6/2008 |
| FR | 2847800 B1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 2001028459 A1 | 4/2001 |
| WO | 2001049213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 2007071436 A2 | 6/2007 |
| WO | 08070797 A2 | 6/2008 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |

OTHER PUBLICATIONS

"Closed Heart Surgery: Back to the Future", Samuel V. Lichtenstein, The Journal of Thoracic and Cardiovascular Surgery, vol. 131, No. 5, May 2006, pp. 941-943.

"Direct-Access Valve Replacement", Christoph H. Huber, et al., Journal of the American College of Cardiology, vol. 46. No. 2, (Jul. 19, 2005).

"Minimally invasive cardiac surgery", M. J. Mack, Surgical Endoscopy, 2006, 20:S488-S492, DOI: 10.1007/s00464-006-0110-8 (presented Mar. 23, 2006).

"Percutaneous Aortic Valve Implantation Retrograde From the Femoral Artery", John G. Webb et al., Circulation, 2006; 113:842-850 (Feb. 6, 2006).

"Percutaneous Aortic Valve Replacement: Resection Before Implantation", Quaden, Rene et al., European J. of Cardio-Thoracic Surgery, vol. 27, No. 5, May 2005, pp. 836-840.

"Transapical aortic valve implantation: an animal feasibility study"; Todd M. Dewey et al., The annals of thoracic surgery 2006; 82: 110-6 (Feb. 13, 2006).

"Transapical Approach for Sutureless Stent-Fixed Aortic Valve Implantation: Experimental Results", Th. Walther et al., European Journal of Cardio-Thoracic Surgery, vol. 29, No. 5, May 2006, pp. 703-708.

"Transapical Transcatheter Aortic Valve Implantation in Humans", Samuel V. Lichtenstein et al., Circulation. 2006; 114: 591-596 (Jul. 31, 2006).

"Transluminal Aortic Valve Placement. A Feasability Study with a Newly Designed Collapsible Aortic Valve", Moazami et al., ASAIO Journal, vol. 42, No. 5, 1996, pp. M381-M385.

"Transluminal Catheter Implanted Prosthetic Heart Valves", Andersen, H. R., International Journal of Angiology, vol. 7, No. 2, Mar. 1998, pp. 102-106.

"Transluminal Implantation of Artificial Heart Valves", Andersen, H. R., et al., European Heart Journal, vol. 13, No. 5, May 1992, pp. 704-708.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Ruiz, Carlos, Overview of PRE-CE Mark Transcatheter Aortic Valve Technologies, Euro PCR—dated May 25, 2010.

Transcatheter Valve Repair, Hijazi et al., CRC Press, Jan. 2006, pp. 165-186.

Extended European Search Report for Appln. No. 21173299.5 mailed Sep. 29, 2021 (pp. 1-14).

* cited by examiner

TRANSCATHETER MITRAL VALVE FIXATION CONCEPTS

CROSS-REFERENCE TO RELATED APPLICATIONS

This application claims the benefit of the filing date of U.S. Provisional Patent Application No. 63/022,647, filed May 11, 2020, the disclosure of which is hereby incorporated herein by reference in its entirety.

BACKGROUND OF THE DISCLOSURE

The present disclosure relates to collapsible prosthetic heart valves, and more particularly, to devices and methods for anchoring collapsible prosthetic heart valves within a native valve annulus.

Prosthetic heart valves that are collapsible to a relatively small circumferential size can be delivered into a patient less invasively than valves that are not collapsible. For example, a collapsible/expandable valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible/expandable prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed to reduce its circumferential size.

When a collapsed prosthetic valve has reached the desired implant site in the patient (e.g., at or near the native annulus of the patient's heart valve that is to be repaired by the prosthetic valve), the prosthetic valve can be deployed or released from the delivery apparatus and expanded to its full operating size. For balloon-expandable valves, this generally involves releasing the entire valve, assuring its proper location, and then expanding a balloon positioned within the valve stent. For self-expanding valves, on the other hand, the stent automatically expands as the stent is withdrawn from the delivery apparatus.

The clinical success of collapsible/expandable heart valves is dependent, in part, on the anchoring of the valve within the native valve annulus. Self-expanding valves typically rely on the radial force exerted by expanding the stent against the native valve annulus to anchor the valve within the native valve annulus. However, if the radial force is too high, the heart tissue may be damaged. If, instead, the radial force is too low, the heart valve may move from its deployed position and/or migrate from the native valve annulus, for example, into the left ventricle.

Movement of the prosthetic heart valve may result in the leakage of blood between the prosthetic heart valve and the native valve annulus. This phenomena is commonly referred to as paravalvular leakage. In mitral valves, paravalvular leakage enables blood to flow from the left ventricle back into the left atrium during systole, resulting in reduced cardiac efficiency and strain on the heart muscle.

Despite the various improvements that have been made to collapsible/expandable prosthetic heart valves, challenges remain in anchoring prosthetic heart valves within the native valve annulus of a patient, especially within the native mitral valve annulus. For example, prosthetic mitral valves often require a low profile so as not to interfere with atrial function, and the low profile complicates securely anchoring the prosthetic heart valve in place. Moreover, the native mitral valve annulus has reduced calcification or plaque compared to the native aortic valve annulus, for example, which can make for a less stable surface to anchor the prosthetic heart valve.

BRIEF SUMMARY OF THE DISCLOSURE

In accordance with a first aspect of the present disclosure, a prosthetic heart valve having a collapsible and expandable frame formed of compliant wires is provided. Among other advantages, the frame is designed to form an indentation at a location at which the frame engages the native valve annulus to form a sub-annular bulge that aids in anchoring the valve within the native annulus and impedes paravalvular leakage.

One embodiment of the prosthetic heart valve includes an expandable stent extending along a longitudinal axis between an inflow end and an outflow end, a valve assembly disposed within the stent and an expandable frame formed of compliant wires. The frame includes a first end coupled to the stent, a second end, and a lumen extending therethrough for receiving the stent, whereby when the frame is expanded in the native valve annulus, the compliant wires form an indented region in the frame between the first and second ends of the body and a sub-annulus portion of the frame forms a bulge.

Another embodiment of the prosthetic heart valve includes an expandable stent having a plurality of struts forming cells, a pivot arm attached to the stent, a valve assembly disposed within the stent and an expandable that forms a lumen extending therethrough for receiving the stent and the valve assembly. The pivot arm is pivotable between a collapsed condition in which the pivot arm lies substantially flush with the stent when the stent is in a collapsed condition and an expanded condition in which the pivot arm extends radially away from stent when the stent is in an expanded condition such that pivoting the pivot arm from the collapsed condition to the expanded condition causes the pivot arm to aid in expanding the frame.

A method of implanting a prosthetic heart valve within a native heart valve annulus is provided herein and includes delivering the prosthetic heart valve within a delivery device in a collapsed condition to a target site adjacent a native valve annulus, expanding the prosthetic heart valve at the target site, whereupon the stent expands and the frame expands into engagement with the native valve annulus, and pressing the frame against the native valve annulus so that an indented region is formed in the frame adjacent the native valve annulus and a portion of the frame below the native valve annulus expands radially outward relative to the indented region.

BRIEF DESCRIPTION OF THE DRAWINGS

Various embodiments of the present disclosure are described herein with reference to the drawings, wherein.

DETAILED DESCRIPTION

Blood flows through the mitral valve from the left atrium to the left ventricle. As used herein in connection with a prosthetic heart valve, the term "inflow end" refers to the end of the heart valve through which blood enters when the valve is functioning as intended, and the term "outflow end" refers to the end of the heart valve through which blood exits when the valve is functioning as intended. Also as used herein, the terms "substantially," "generally," and "about" are intended to mean that slight deviations from absolute are included within the scope of the term so modified.

Figure 1:
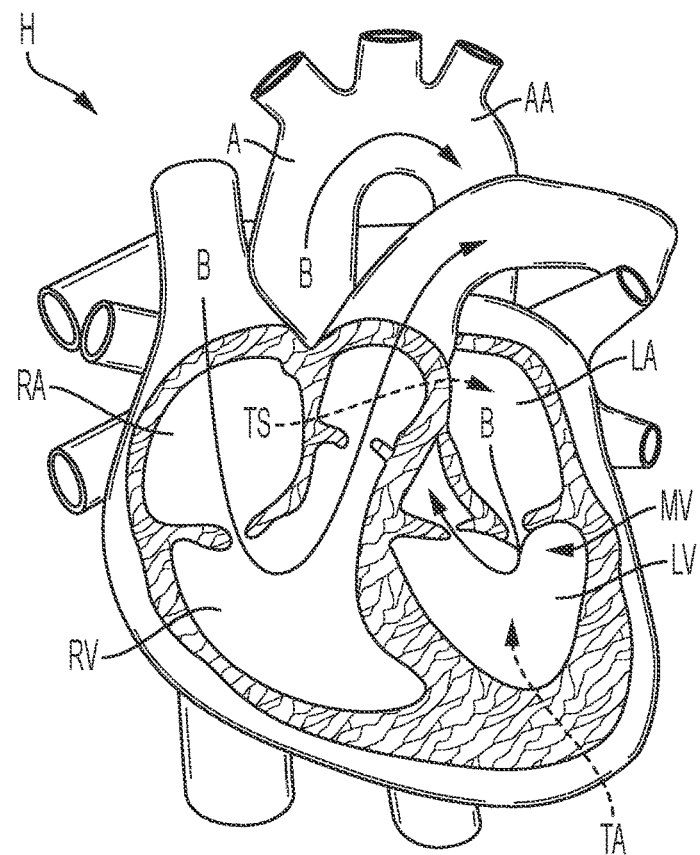
FIG. 1 is a highly schematic cutaway view of the human heart, showing two approaches for delivering a prosthetic mitral valve to an implantation site.

FIG. 1 is a schematic cutaway representation of a human heart H. The human heart includes two atria and two ventricles: right atrium RA and left atrium LA, and right ventricle RV and left ventricle LV. Heart H further includes aorta A and aortic arch AA. Disposed between the left atrium and the left ventricle is mitral valve MV. The mitral valve, also known as the bicuspid valve or left atrioventricular valve, is a dual-flap that opens as a result of increased pressure in left atrium LA as it fills with blood. As atrial pressure increases above that in left ventricle LV, mitral valve MV opens and blood flows into the left ventricle. Blood flows through heart H in the direction shown by arrows "B".

A dashed arrow, labeled "TA", indicates a transapical approach of implanting a prosthetic heart valve, in this case to replace the mitral valve. In the transapical approach, a small incision is made between the ribs of the patient and into the apex of left ventricle LV to deliver the prosthetic heart valve to the target site. A second dashed arrow, labeled "TS", indicates a transseptal approach of implanting a prosthetic heart valve in which the valve is passed through the septum between right atrium RA and left atrium LA. Other approaches for implanting a prosthetic heart valve are also possible and may be used to implant the collapsible prosthetic heart valve described in the present disclosure.

Figure 2:
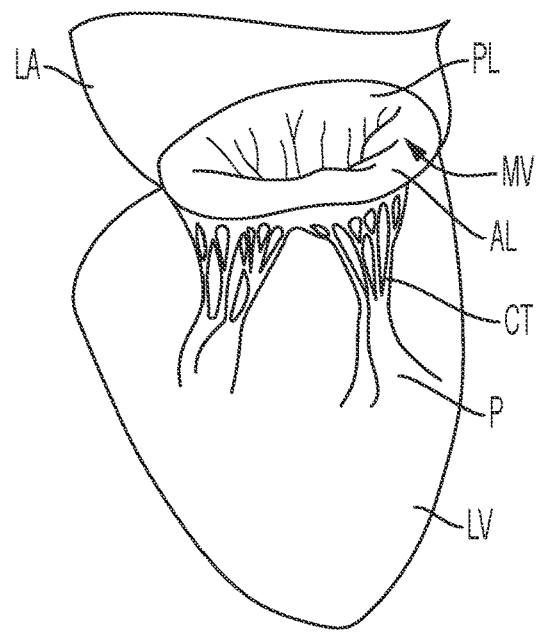
FIG. 2 is a highly schematic representation of a native mitral valve and associated cardiac structures.

FIG. 2 is a more detailed schematic representation of native mitral valve MV and its associated structures. As previously noted, mitral valve MV includes two flaps or leaflets, posterior leaflet PL and anterior leaflet AL, disposed between left atrium LA and left ventricle LV. Cord-like tendons, known as chordae-tendineae CT, connect the two leaflets to the medial and lateral papillary muscles P. During atrial systole, blood flows from higher pressure in left atrium LA to lower pressure in left ventricle LV. When left ventricle LV contracts during ventricular systole, the increased blood pressure in the chamber pushes the posterior and anterior leaflets to close, preventing the backflow of blood into left atrium LA. Since the blood pressure in left atrium LA is much lower than that in left ventricle LV, the leaflets attempt to evert to low pressure regions. Chordae tendineae CT prevent the eversion by becoming tense, thus pulling on the leaflets and holding them in the closed position.

Figure 3A:
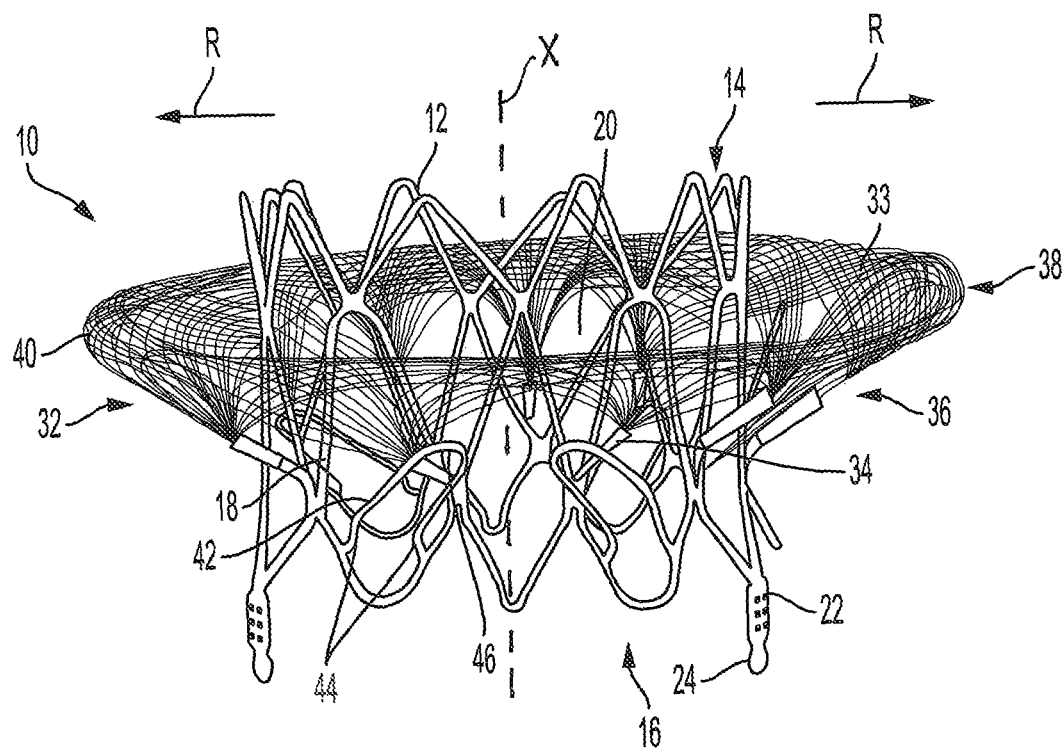
FIG. 3A is a side elevational view of a frame formed of compliant wires coupled by a clamp to a stent of a prosthetic heart valve according to an embodiment of the present disclosure.
Figure 3B:
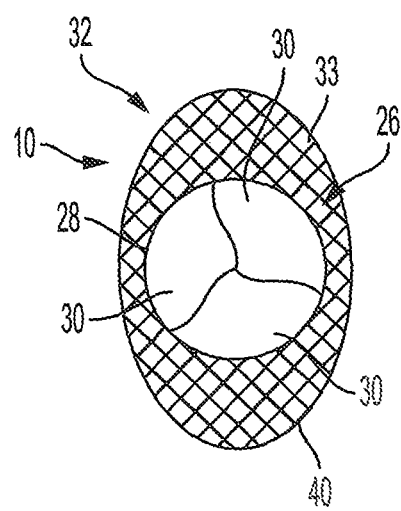
FIG. 3B is a highly schematic end view of a valve assembly disposed within the stent and frame of FIG. 3A.

Prosthetic heart valve 10, as shown in FIGS. 3A and 3B, is a collapsible and expandable prosthetic heart valve designed to replace the function of the native mitral valve MV (shown in FIGS. 1-2) of a patient. For balloon-expandable variants, prosthetic heart valve 10 may be expandable, but not collapsible, or not readily collapsible. When used to replace native mitral valve MV, prosthetic valve 10 may have a low profile so as not to interfere with the heart's electrical conduction system pathways or the atrial function.

Prosthetic heart valve 10 includes a stent 12, which may be formed from biocompatible materials that are capable of self-expansion, for example, shape-memory alloys such as nitinol. Alternatively, stent 12 may be balloon expandable or expandable by another force exerted radially outward on the stent. When expanded, stent 12 may exert a radial force in the direction of arrows R to assist in stabilizing prosthetic heart valve 10 within the native mitral valve annulus.

Stent 12 extends along a longitudinal axis "X" between an inflow end 14 and an outflow end 16, and may be substantially cylindrical in shape. Stent 12 may include a plurality of struts 18 that form cells 20 connected to one another in one or more annular rows circumferentially extending about the stent. In one example, stent 12 is formed by laser cutting a predetermined pattern into a metallic tube. Cells 20 may be substantially the same size around the perimeter of stent 12 and along the length of the stent. Alternatively, cells 20 near inflow end 14 may be larger than the cells near outflow end 16. When stent 12 is expanded, struts 18 forming a cell 20 in the annular row of cells adjacent the outflow end 16 of the stent may bend about the midsection of the cell (e.g., in a direction orthogonal to the longitudinal axis), as shown in FIG. 3A, such that the lower apex of the cell extends radially outward relative to the midsection of the cell, and the upper apex of the cell extends radially outward relative to the midsection of the cell.

A plurality of commissure attachment features 22 may be provided on stent 12 for attaching the commissure between two adjacent leaflets to the stent. As shown in FIG. 3A, commissure attachment features 22 may lie at the intersection of two struts 18 that form one cell 20 at the outflow end 16 of stent 12. Commissure attachment features 22 may include one or more eyelets that facilitate the suturing of the leaflet commissure to stent 12.

One or more retaining elements 24 may be provided at the outflow end 16 of the stent 12. As shown in FIG. 3A, retaining elements 24 may extend from commissure attachment features 22. Retaining elements 24 are sized to cooperate with a corresponding retaining structure on a delivery device (not shown) for delivering prosthetic heart valve 10 into the patient. This cooperation minimizes the axial movement of prosthetic heart valve 10 relative to the delivery device during unsheathing or resheathing procedures, and minimizes rotation of the prosthetic heart valve relative to the delivery device as the delivery device is advanced to the target location and during deployment.

With additional reference to FIG. 3B, prosthetic heart valve 10 also includes a valve assembly 26, which may be secured to stent 12 by suturing the valve assembly to struts 18 and/or to commissure attachment features 22. In order to more clearly illustrate stent 12 and the additional features described below, valve assembly 26 is not illustrated in FIG. 3A. It will be understood, however, that assembled prosthetic heart valve 10 includes the valve assembly described below and schematically illustrated in FIG. 3B.

Valve assembly 26 includes a cuff 28 and a plurality of leaflets 30 that open and close collectively to function as a one-way valve. Both cuff 28 and leaflets 30 may be wholly or partly formed of any suitable biological material, such as bovine or porcine pericardium, or biocompatible polymer, such as polytetrafluorethylene (PTFE), urethanes and the like. Prosthetic heart valve 10 may also include a sealing skirt (not shown) disposed about an abluminal surface of stent 12. When prosthetic heart valve 10 is implanted within the native mitral valve annulus of a patient, the sealing skirt may seal any gaps between the prosthetic heart valve and the native mitral valve annulus to help prevent the backflow of blood into left atrium LA. The sealing skirt may also be formed of any suitable biological material, such as bovine or porcine pericardium, or biocompatible polymer, such as PTFE, urethanes or similar materials.

Prosthetic heart valve 10 may also include one or more engagement arms 42 circumferentially mounted around stent 12 to engage tissue and stabilize the prosthetic heart valve within the native mitral valve annulus. Engagement arms 42 may be pivotally mounted to stent 12 so as to be transitionable from a collapsed condition in which the engagement arms lie against or within the cells 20 of the collapsed stent during delivery of prosthetic heart valve 10 into the patient, to an expanded condition in which the engagement arms extend radially outward from the stent after the prosthetic heart valve has been deployed from the delivery device. As illustrated in FIG. 3A, each engagement arm 42 may include two arm segments that are attached at ends 44 to two struts 18 forming a single cell 20, with a looped portion 46 connecting the other ends of the arm segments together. Thus, when engagement arms 42 are in the collapsed condition, each engagement arm is completely disposed within a predetermined one of the cells 20 of stent 12 and lies flush with the stent. Engagement arms 42 may be arranged in any of cells 20, for example, within every other cell within the annular row adjacent to the outflow end 16 of stent 12, as shown in FIG. 3A.

Prosthetic heart valve 10 may be used to repair a malfunctioning native heart valve, such as a native mitral valve, or an implanted and malfunctioning prosthetic heart valve. When implanted within the native mitral valve annulus, prosthetic heart valve 10 is designed to replace the function of the native mitral valve. The prosthetic heart valve may be delivered to a desired site (e.g., near the native mitral valve annulus) using any suitable delivery device (not shown) such as a catheter, a trocar, a laparoscopic instrument, or the like. During delivery, prosthetic heart valve 10 may be disposed inside the delivery device in the collapsed configuration. The delivery device may be introduced into the patient using a transapical, transseptal or other percutaneous approach and delivered toward the native mitral valve.

Once the delivery device has reached the target site, a physician may unsheathe prosthetic heart valve 10 to allow the prosthetic heart valve to expand from the collapsed condition to the expanded condition and engage tissue, thereby anchoring the prosthetic heart valve within the native mitral valve annulus. When prosthetic heart valve 10 is deployed, stent 12 will be outwardly expanded until it contacts the native valve annulus, such as the mitral valve annulus. Cells 20 in the annular row of cells adjacent the outflow end 16 of stent 12 may bend about their midsection such that, when properly positioned, the upper apex of each cell extends outwardly against a portion of the annulus proximate the atrium, and the lower apex of each cells extends outwardly and against a portion of the annulus proximate the ventricle. Further, each of engagement arms 42 may expand as stent 12 expands. More particularly, engagement arms 42 may transition from the collapsed condition in which they lie against or within cells 20 of stent 12 to the expanded condition in which each one of the engagement arms pivots outwardly from the stent to capture the posterior leaflet PL and the anterior leaflet AL and provide further anchoring support. Collectively, all of these features are intended to anchor prosthetic heart valve 10 within the mitral valve annulus.

Additional features to more securely anchor and stabilize prosthetic heart valve 10 within the mitral valve annulus are desirable. In one embodiment, prosthetic heart valve 10 also includes a collapsible and an expandable frame 32 defining a lumen for receiving stent 12 and valve assembly 26. Frame 32 may include a plurality of wires or braided strands 33 (collectively hereinafter "wires") formed from compliant biocompatible materials that are capable of self-expansion, for example, shape-memory alloys such as nitinol. Alternatively, frame 32 may be formed from a balloon expandable or other mechanically expandable and compliant material. Clamps 34 couple a first end 36 of frame 32 to stent 12. As shown in FIG. 3A, clamps 34 may be attached at one end to struts 18 and may lie between two adjacent cells 20 positioned in the same annular row adjacent to the outflow end 16 of stent 12. A plurality of wires 33 may be grouped together and secured within the other end of clamps 34, thus forming scallops adjacent the first end 36 of frame 32. The scalloped portion S prevents frame 32 from interfering with blood flow through the outflow end 16 of stent 12 to the left ventricular outflow tract of the heart.

Frame 32 may flare outwardly relative to the longitudinal axis of stent 12 from the first end 36 of the frame to a radially extending flange 40 at a second end 38 of the frame. The second end 38 of frame 32 may be disposed about a midsection of stent 12. Flange 40 is designed to at least partially project into the left atrium of the heart and to anchor stent 12 against the atrium-facing surface of the native mitral valve annulus of the patient. As shown in FIG. 3A, the flange 40 of frame 32 may have a transverse cross-section that is greater than the transverse cross-section of the body 41 of the frame. Referring to FIG. 3B, the flange 40 of frame 32 may have an elliptical or other non-circular transverse cross-section.

When expanded, frame 32 extends radially outward at an angle from stent 12. In one embodiment, the angle formed between frame 32 and stent 12 is between approximately 45 degrees and approximately 75 degrees, and may be about 60 degrees. The wires 33 of frame 32 are preferably designed to exhibit a higher compliance than stent 12. In this manner, frame 32 may expand to a greater diameter than stent 12 to assist in anchoring prosthetic heart valve 10 within the native heart valve annulus, without damaging the heart tissue that is contacted by the frame.

Figure 7:
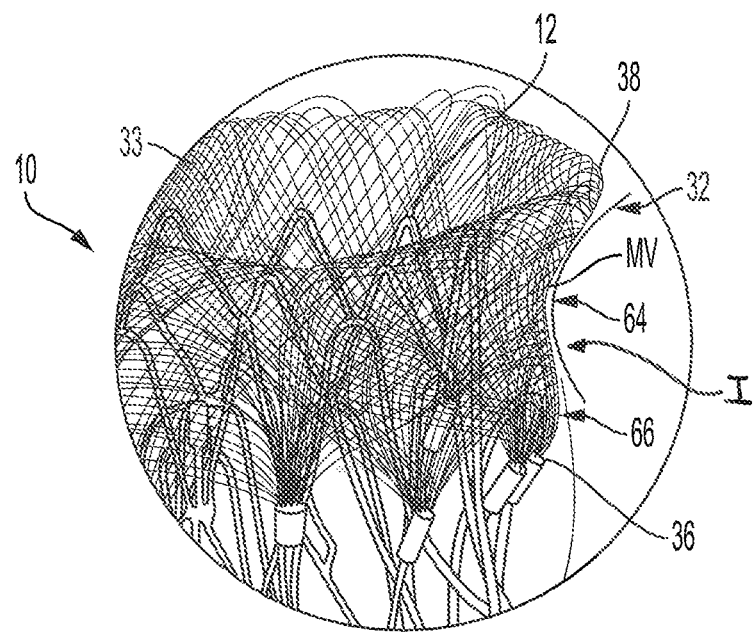
FIG. 7 is a highly schematic view showing the prosthetic heart valve of FIG. 3A implanted within the native mitral valve annulus of a patient.

During deployment of prosthetic heart valve 10, frame 32 may self-expand simultaneously with the expansion of stent 12 and project radially outward from an abluminal surface of the stent to engage with the native annulus of mitral valve MV. As shown in FIG. 7, the compliant wires 33 of frame 32 may compress in a radially inward direction in a region, identified by the arrow labeled 64, at which the frame engages the native valve annulus. Engagement region 64 is preferably a location spaced from the first end 36 of frame 32 and the second end 38 of the frame, and may be approximately at the midsection of the frame. In this manner, the highly compliant wires 33 located between engagement region 64 and the first end 36 of frame 32 will form a sub-annulus bulge 66 at a location inferior to the native mitral annulus and within the left ventricle. The combination of sub-annulus bulge 66 and the enlarged second end 38 of frame 32 thus forms indented region I which sandwiches the native mitral valve annulus and anchors prosthetic valve 10 within the valve annulus. Due to the highly compliant wires 33, frame 32 does not exhibit a radial force against the native heart tissue that is large enough to damage the tissue.

The wires 33 of expanded frame 32 may also fill voids between the sealing skirt of the prosthetic heart valve and the native mitral valve annulus, particularly at the sub-annulus bulge 66, when the prosthetic heart valve has been implanted in the native mitral valve annulus. As a result, the wires 33 of frame 32 may fill irregularities in the native mitral valve annulus and prevent paravalvular leakage between prosthetic heart valve 10 and the native mitral valve annulus.

Figure 4:
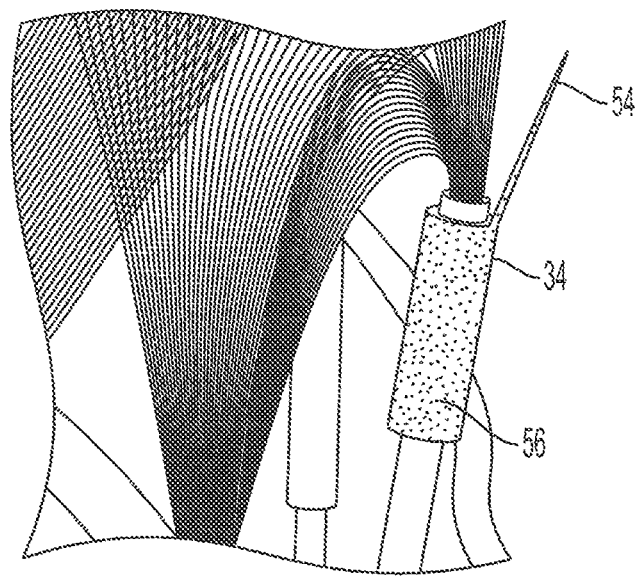
FIG. 4 is an enlarged view of the clamp shown in FIG. 3A.

In another embodiment, prosthetic heart valve 10 may include one or more prongs or cleats 54 having a sharpened tip that penetrates tissue at or near the native valve annulus when the prosthetic heart valve is expanded. In one embodiment, prongs 54 may be provided on one or more of clamps 34, as shown in FIG. 4. In other embodiments, prongs 54 may be provided on stent 12, frame 32 and/or engagement arms 42.

Figure 5:
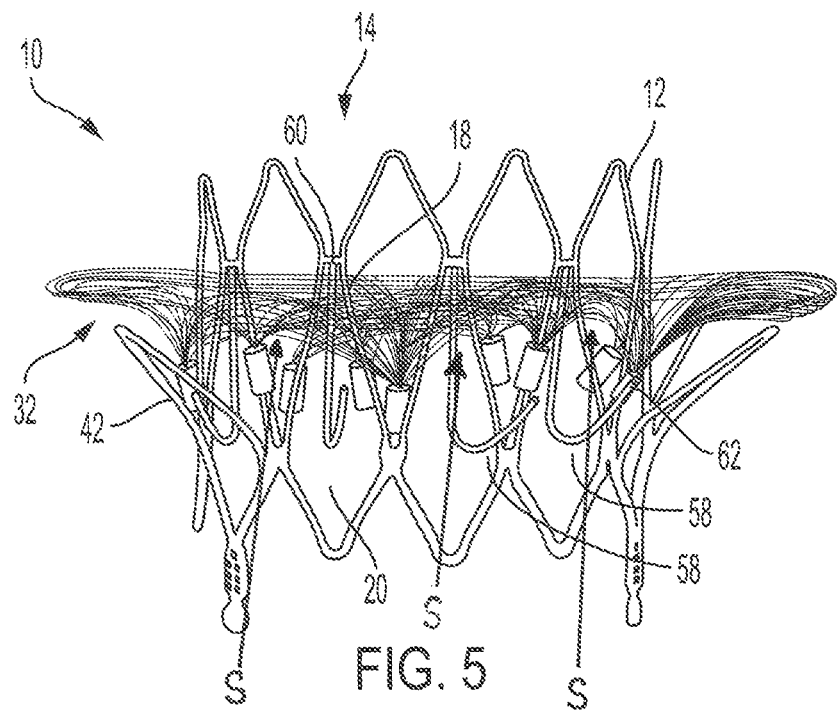
FIG. 5 is a side elevational view showing hooks disposed around the prosthetic heart valve stent of FIG. 3A.

Referring to FIG. 5, in another embodiment, prosthetic heart valve 10 may include a plurality of collapsible and expandable hooks 58 mounted about the circumference of stent 12. Each hook 58 may include an attached end 60 that lies at the intersection of two struts 18 that form one cell 20 at the inflow end 14 of stent 12. Each hook 58 may then extend in the longitudinal direction of stent 12 through the scalloped portion of frame 32, terminating at an outwardly curved end 62 at about the midsection of stent 12. In this manner, the curved ends 62 of hooks 58 are positioned to wrap around and capture posterior leaflet PL and anterior leaflet AL when prosthetic heart valve 10 is anchored within the native annulus of mitral valve MV (FIG. 2). As shown in FIG. 5, engagement arms 42 may be attached only to cells 20 that do not include hooks 58. For example, engagement arms 42 may be attached to cells aligned in the longitudinal direction of stent 12 with commissure attachment features 22, while the other cells disposed between adjacent commissure attachment features in the circumferential direction of the stent may include hooks 58. Nevertheless, alternative arrangements are possible.

When prosthetic heart valve 10 is expanded within the native heart valve, such as the native mitral valve MV, hooks 58 may also expand and wrap around and capture posterior leaflet PL and anterior leaflet AL to further anchor the prosthetic heart in place within the native mitral valve annulus.

In yet another embodiment, the surface of any of the tissue engaging features of prosthetic heart valve 10, such as stent 12, frame 32, engagement arms 42, clamps 34 and/or hooks 58, may be modified to include friction inducing elements 56 that increase the frictional forces between the surface of the feature and the heart tissue of the patient when the prosthetic heart valve is implanted within the native heart valve annulus. The friction inducing elements 56 may be any micro or macro surface modifications such as cleats, protrusions, ridges and the like. Because the friction-inducing elements 56 are shown in FIG. 4 on a micro scale, the friction-inducing elements are illustrated as stippling. Thus, when prosthetic heart valve 10 is implanted within a native valve annulus, the prosthetic heart valve is less likely to move within or migrate from the native valve annulus due to the increased friction between the modified surface regions and the native heart valve tissue.

Figure 6:
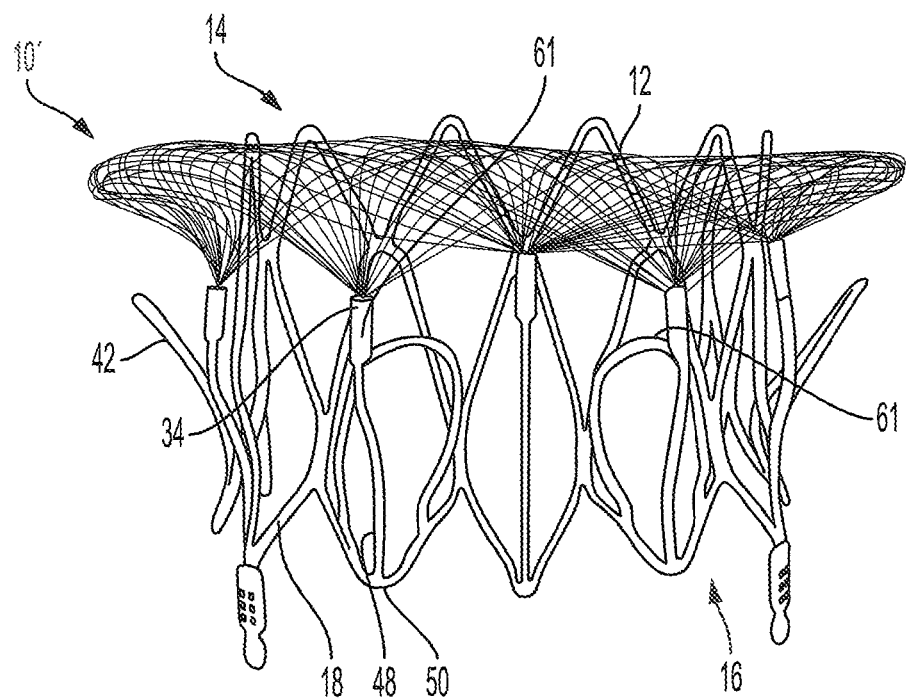
FIG. 6 is a side elevational view of a prosthetic heart valve stent having pivot arms coupled to a frame formed of compliant wires according to a variant of the present disclosure.

FIG. 6 illustrates a variant prosthetic heart valve 10' that may include any one or more of the features of prosthetic heart valve 10, except as described below. Each clamp 34 of prosthetic heart valve 10' is coupled to stent 12 by a secondary strut 48 extending generally in the longitudinal direction of the stent from a first end 50 at the outflow end 16 of the stent to a second end 52 closer to the inflow end 14 of the stent. The first end 50 of each secondary strut 48 may be attached to the intersection of two struts 18 forming the lower apex of a cell 20 in the annular row of cells adjacent the outflow end 16 of the stent. Clamps 34 may be attached to the second ends 52 of secondary struts 48 such that the clamps are disposed adjacent the upper apex of the same cell 20 to which the first end 50 of the secondary strut is attached. Clamps 34 are thus positioned relatively closer to the inflow end 14 of stent 12 than in the embodiment illustrated in FIG. 3A. As a result of the higher positions of clamps 34, frame 32 is positioned relatively closer to, or at, the inflow end 14 of stent 12, relative to the frame of prosthetic heart valve 10 shown in FIG. 3A. The second end 52 of each secondary strut 48 and, in turn, each clamp 34 is positioned radially outward from stent 12 and is not attached to the stent.

Variant prosthetic heart valve 10' may also include one or more pivot arms 61 circumferentially mounted around stent 12 to assist in expanding frame 32 and stabilizing the prosthetic heart valve within the native mitral valve annulus. Pivot arms 61 may be pivotally mounted to stent 12 so as to be transitionable from a collapsed condition in which the pivot arms lie against or within the cells 20 of the collapsed stent during delivery of prosthetic heart valve 10 into the patient, to an expanded condition in which the pivot arms extend radially outward from the stent after the prosthetic heart valve has been deployed from the delivery device. As illustrated in FIG. 6, each pivot arm 61 may include two segments that are attached to two struts 18 forming a single cell 20, and a looped portion connecting the two segments together. Thus, when pivot arms 61 are in the collapsed condition, each pivot arm is completely disposed within a predetermined one of the cells 20 of stent 12, or lies substantially flush against the stent. Pivot arms 61 are disposed between secondary struts 48 and stent 12 in the radial direction of the stent. The pivot arms are strong enough to push secondary struts 48 and/or clamps 34 radially outward when the pivot arms expand and contact the secondary struts and/or clamps to assist in expanding the frame during deployment of prosthetic heart valve 10'. Furthermore, pivot arms 61 may continue to apply a radial outward force on secondary struts 48 and/or clamps 34 after prosthetic valve 10' has been expanded such that frame 32 is secured against the native mitral valve annulus after the prosthetic heart valve has been implanted within the native valve annulus.

Any of the above described stabilization features, including expandable frame 32, engagement arms 42, prongs 54, friction inducing elements 56, hooks 58, or pivot arms 61 may be individually incorporated into a prosthetic heart valve or may be incorporated into a prosthetic heart valve in combination with any one or more of the other stabilization features described herein.

After prosthetic heart valve 10, 10' has been properly positioned and anchored within the native mitral valve annulus of a patient, the prosthetic heart valve may work as a one-way valve to restore proper function of the heart valve by allowing blood to flow in one direction (e.g., from the left atrium to the left ventricle) while preventing blood from flowing in the opposite direction.

To summarize the foregoing, a prosthetic heart valve includes an expandable stent extending along a longitudinal axis between an inflow end and an outflow end; a valve assembly disposed within the stent; and a collapsible and expandable frame formed of compliant wires, the frame having a body including a first end coupled to the stent, a second end, and a lumen extending therethrough for receiving the stent, whereby when the frame is expanded in the native valve annulus, the compliant wires form an indented region in the frame between the first and second ends of the body and a sub-annulus portion of the frame forms a bulge; and/or when the frame is expanded, the body of the frame may extend away from the longitudinal axis; and/or the body of the frame may form an angle with the stent of between approximately 45 degrees and approximately 75 degrees; and/or the body of the frame may form an angle with the stent of approximately 60 degrees; and/or the frame may include a flange at the second end of the body, and the flange may have a transverse cross-section greater than a transverse cross-section of the body; and/or the stent may include a pivot arm pivotable between a collapsed condition in which the pivot arm lies flush with the stent when the stent is in an expanded condition and an expanded condition in which the pivot arm extends radially away from the stent when the stent is in the expanded condition; and/or the stent may include a plurality of the pivot arms circumferentially disposed about the stent; and/or the frame may be coupled to the plurality of pivot arms; and/or the prosthetic heart valve may further include a plurality of clamps coupling the frame to the stent; and/or at least one of the plurality of clamps may include a prong to anchor into tissue; and/or a surface of at least one of the plurality of clamps may include a plurality of friction-inducing elements; and/or the prosthetic heart valve may further include a plurality of expandable hooks disposed circumferentially about the stent for capturing native leaflets; and/or the frame may include a scalloped portion facing toward the outflow end of the stent.

In another embodiment, a prosthetic heart valve includes an expandable stent including a plurality of struts forming cells; a pivot arm attached to the stent, the pivot arm being pivotable between a collapsed condition in which the pivot arm lies substantially flush with the stent when the stent is in an expanded condition and an expanded condition in which the pivot arm extends radially away from stent when the stent is in the expanded condition; a valve assembly disposed within the stent; and a collapsible and expandable frame formed of wires, the frame having a body forming a lumen extending therethrough for receiving the stent and the valve assembly, the body being coupled to the stent such that pivoting the pivot arm from the collapsed condition to the expanded condition causes the pivot arm to aid in expanding the frame; and/or the prosthetic heart valve may further include a secondary strut connected to a predetermined one of the cells and an attachment member coupling the frame to the secondary strut, wherein when the pivot arm is in the expanded condition, the pivot arm exerts an outward radial force on at least one of the secondary strut or the attachment member; and/or the pivot arm may be disposed at least partially within the predetermined one of the cells; and/or the secondary strut may extend along a midline of the predetermined one of the cells in a direction substantially parallel to a longitudinal axis of the stent.

Yet another embodiment provides a method of deploying a prosthetic heart valve at a target site, the prosthetic heart valve including an expandable stent having an inflow end and an outflow end, a valve assembly disposed within the stent, and a collapsible and expandable frame coupled to and surrounding the stent. The method includes delivering the prosthetic heart valve within a delivery device in a collapsed condition to a target site adjacent a native valve annulus; expanding the prosthetic heart valve at the target site, whereupon the stent expands and the frame expands into engagement with the native valve annulus; and pressing the frame against the native valve annulus so that an indented region is formed in the frame adjacent the native valve annulus and a portion of the frame below the native valve annulus expands radially outward relative to the indented region; and/or the expanding step may include expanding a pivot arm attached to the stent from a collapsed condition to an expanded condition, whereupon the pivot arm contacts an attachment member coupling the frame to the stent; and/or the native valve annulus may be the mitral valve annulus of a patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present disclosure as defined by the appended claims.

The invention claimed is:

1. A prosthetic heart valve, comprising:
an expandable stent extending in first and second longitudinal directions along a longitudinal axis between an inflow end and an outflow end, the stent having a midsection between the inflow end and the outflow end, a plurality of commissure attachment features at the outflow end, and a plurality of struts forming cells connected to one another in one or more annular rows extending circumferentially about the stent;
a plurality of pivot arms circumferentially disposed about the stent, each pivot arm being pivotable between a collapsed condition in which the pivot arm lies within one of the cells when the pivot arm is in a collapsed condition and an expanded condition in which the pivot arm extends radially away from the stent when the stent is in an expanded condition;
a valve assembly disposed within the stent; and
a collapsible and expandable frame formed of compliant wires, the frame having a body including a first end at which a plurality of the wires are joined together in groups, each of the groups being coupled to the stent between adjacent cells in an annular row of cells adjacent the outflow end of the stent and at a position spaced in the first longitudinal direction from the outflow end of the stent and from the commissure attachment features such that the frame in an expanded condition does not overlap in the first and second longitudinal directions with the commissure attachment features, the body including a second end spaced in the second longitudinal direction from the inflow end of the stent and positioned farther in the first longitudinal direction than the first end from the outflow end of the stent and from the commissure attachment features, a flange at the second end, and a lumen extending through the body for receiving the stent, the flange being positioned at the midsection of the stent between the first end of the frame and the inflow end of the stent, the flange in the expanded condition of the frame having a transverse cross-section greater than a transverse cross-section of the body, whereby when the frame is in the expanded condition in the native valve annulus, the compliant wires form an indented region in the frame between the first and second ends of the body and a sub-annulus portion of the frame forms a bulge, and wherein each pivot arm is connected to the stent at a pivot point, the pivot point being positioned between the outflow end of the stent and the first end of the body of the frame.

2. The prosthetic heart valve of claim 1, wherein when the frame is in the expanded condition, the body of the frame extends away from the longitudinal axis.

3. The prosthetic heart valve of claim 2, wherein the body of the frame forms an angle with the stent of between approximately 45 degrees and approximately 75 degrees.

4. The prosthetic heart valve of claim 2, wherein the body of the frame forms an angle with the stent of approximately 60 degrees.

5. The prosthetic heart valve of claim 1, wherein the frame is coupled to the plurality of pivot arms.

6. The prosthetic heart valve of claim 1, further comprising a plurality of clamps coupling the frame to the stent.

7. The prosthetic heart valve of claim 6, wherein at least one of the plurality of clamps includes a prong to anchor into tissue.

8. The prosthetic heart valve of claim 6, wherein a surface of at least one of the plurality of clamps includes a plurality of friction-inducing elements.

9. The prosthetic heart valve of claim 1, further comprising a plurality of expandable hooks disposed circumferentially about the stent for capturing native leaflets.

10. The prosthetic heart valve of claim 1, wherein the frame includes a scalloped portion facing toward the outflow end of the stent.

11. The prosthetic heart valve of claim 1, wherein the frame is coupled to the stent at a spaced distance from both the inflow end of the stent and the outflow end of the stent.

12. The prosthetic heart valve as claimed in claim 1, wherein the stent further includes a plurality of secondary struts, one end of each secondary strut being connected to the stent and another end of each secondary strut being connected to the first end of the body of the frame, whereby the movement of the pivot arms from the collapsed condition to the expanded condition exerts a force on the secondary struts that is radially outward from the stent.

* * * * *